United States Patent [19]

Jonas et al.

[11] 4,016,281
[45] Apr. 5, 1977

[54] TETRALONE AND INDANONE COMPOUNDS

[75] Inventors: Rochus Jonas; Jürgen Uhl; Helmut Müller-Calgan; Klaus Irmscher, all of Darmstadt, Germany

[73] Assignee: Merck Patent Gesellschaft mit beschrankter Haftung, Darmstadt, Germany

[22] Filed: Feb. 18, 1976

[21] Appl. No.: 659,132

[30] Foreign Application Priority Data

Feb. 22, 1975 Germany .............................. 2507782
Dec. 13, 1975 Germany .............................. 2556196

[52] U.S. Cl. .......................... 424/267; 260/293.58; 260/293.62; 260/293.84
[51] Int. Cl.² ......................................... C07D 211/52
[58] Field of Search ................ 260/293.58, 293.62; 424/267

[56] References Cited
UNITED STATES PATENTS

| | | | |
|---|---|---|---|
| 2,820,817 | 1/1958 | Sam | 260/490 |
| 3,547,923 | 12/1970 | Standridge et al. | 260/268 |
| 3,576,811 | 4/1971 | Fusco et al. | 260/294.7 |
| 3,644,372 | 2/1972 | Paragamian | 260/293.56 |
| 3,850,935 | 11/1974 | Nakao et al. | 260/293.52 |
| 3,974,212 | 8/1976 | Cragoe et al. | 260/519 |

Primary Examiner—G. Thomas Todd
Attorney, Agent, or Firm—Millen & White

[57] ABSTRACT

Tetralone and indanone compounds of the formula

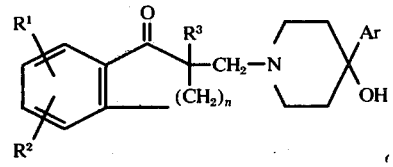

wherein $R^1$ is H, OH, alkoxy of 1–4 carbon atoms, cycloalkoxy of 3–6 carbon atoms, F, Cl, Br, $NO_2$, monoalkylamino or dialkylamino, wherein each alkyl is of 1–4 carbon atoms, alkanoyloxy of 1–6 carbon atoms or alkanoylamino of 1–4 carbon atoms; $R^2$ is OH or alkoxy of 1–4 carbon atoms or $R^1$ and $R^2$ collectively are methylenedioxy; $R^3$ is H or $CH_3$; Ar is phenyl or phenyl substituted by up to 5 of alkyl of 1–4 carbon atoms, alkoxy of 1–4 carbon atoms, F, Cl, Br or $CF_3$; n is 1 or 2, and physiologically acceptable acid addition salts thereof, are central nervous system depressants.

29 Claims, No Drawings

TETRALONE AND INDANONE COMPOUNDS

BACKGROUND OF THE INVENTION

This invention relates to novel tetralone and indanone compounds.

SUMMARY OF THE INVENTION

In one composition aspect, this invention relates to indanone and tetralone compounds of Formula I,

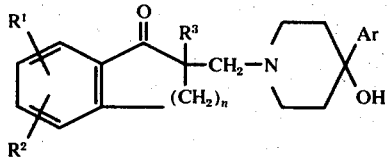

wherein $R^1$ is H, OH, alkoxy of 1–4 carbon atoms, cycloalkoxy of 3–6 carbon atoms, F, Cl, Br, $NO_2$, $NH_2$, monoalkylamino or dialkylamino, wherein the alkyl each are of 1–4 carbon atoms, alkanoyloxy of 1–6 carbon atoms, or alkanoylamino of 1–4 carbon atoms; $R^2$ is H, OH or alkoxy of 1–4 carbon atoms or $R^1$ and $R^2$ collectively are methylenedioxy; $R^3$ is H or $CH_3$; Ar is phenyl or phenyl substituted by up to 5 of alkyl or alkoxy of 1–4 carbon atoms, F, Cl, Br, or $CF_3$; n is 1 or 2, and pharmaceutically acceptable acid addition salts thereof.

In another aspect, this invention relates to a process for preparing tetralone and indanone compounds of Formula I and their physiologically acceptable acid addition salts, wherein a. a phenylpiperidine compound of Formula II

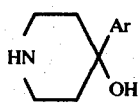

wherein Ar is as above or an acid addition salt thereof is reacted with a ketone of Formula III

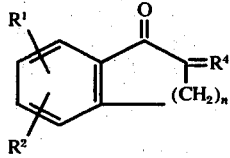

wherein $R^4$ is $(H,R^3)$, $CH_2$, $(R^3,CH_2X)$ or $(R^3,CH_2NR^5R^6)$; X is Cl, Br, OH or functionally modified OH and $R^5$ and $R^6$ each are alkyl of 1–4 carbon atoms and $R^1$, $R^2$, $R^3$ and n are as above or with one of its functional derivatives, and, if $R^4$ is $(H,R^3)$, the ketone is formaldehyde or a formaldehyde donor;

b. a carboxylic acid of Formula IV

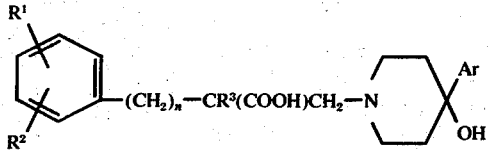

wherein $R^1$, $R^2$, $R^3$, Ar and n are as above or a functional acid derivative thereof is treated with a cyclizing agent;

c. a compound of Formula V

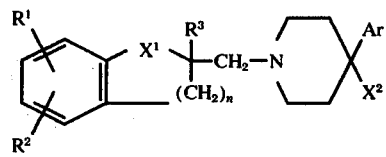

wherein $X^1$ is a free or functionally-modified carbonyl group; $X^2$ is Cl, Br or I, or, if $X^1$ is a functionally-modified carbonyl group, is OH; and $R^1$, $R^2$, $R^3$, Ar and n are as above, is treated with a solvolyzing agent;

d. an aminoketone of Formula VI

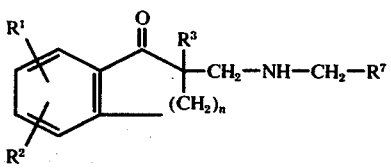

wherein $R^7$ is $-CH_2-C(=CH_2)$ -Ar or $-CH=C(CH_3)$-Ar and $R^1$, $R^2$, $R^3$, Ar and n are as above, is treated with formaldehyde;

e. an enaminoketone of Formula VII

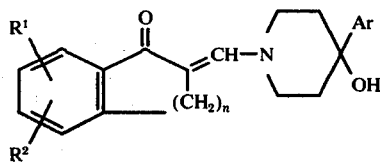

wherein $R^1$, $R^2$, Ar and n are as above, is treated with a reducing agent;

f. a tetralol or indanol compound of Formula VIII

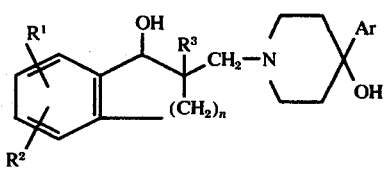

wherein $R^1$, $R^2$, $R^3$, Ar and n are as above, is treated with an oxidizing agent; and, if appropriate, one or more of $R^1$, $R^2$, and/or Ar in a resulting compound of Formula I are converted into one or more other $R^1$, $R^2$ and/or Ar by treatment with a reducing, alkylating and/or acylating agent and/or by diazotization and subsequent treatment with a halogen compound or a solvolyzing agent, and/or a compound of Formula I is converted into one if its pharmaceutically-acceptable acid addition salts by treatment with an acid and/or a compound of Formula I is liberated from one of its acid addition salts by treatment with a base.

DETAILED DESCRIPTION $R^1$ is H, OH, alkoxy of 1–4 carbon atoms, cycloalkoxy of 3–6 carbon atoms, F, Cl, Br, $NO_2$, monoalkylamino or dialkylamino, wherein each alkyl is of 1–4 carbon atoms, alkanoyloxy of 1–6 carbon atoms or alkanoylamino of 1–4 carbon atoms.

Exemplary of alkyl functions in the foregoing are methyl, ethyl, n-propyl, isopropyl, n-butyl, isobutyl, sec.-butyl and tert.-butyl. Methyl and ethyl are preferred. Monoalkylamino is preferably methylamino or ethylamino and dialkylamino is dimethylamino, methylethylamino or diethylamino.

Alkoxy includes methoxy, ethoxy, n-propoxy, isopropoxy, n-butoxy, isobutoxy, sec.-butoxy and tert.-butoxy, but methoxy and ethoxy are preferred.

Alkanoyloxy includes formyloxy, acetoxy, propionoxy, butyryloxy, isobutyryloxy, valeryloxy, isovaleryloxy, trimethylacetoxy, capronyloxy or tert.-butylacetoxy. Acetoxy and propionoxy are preferred.

Cycloalkoxy includes cyclopropyloxy, cyclobutyloxy, cyclopentyloxy, 1-, 2-, or 3-methylcyclopentyloxy and cyclohexyloxy. Cyclopentyloxy and cyclohexyloxy are preferred.

Alkanoylamino includes formamido, acetamido, propionamido, butyramido and isobutyramido. Acetamido is preferred.

$R^1$ and $R^2$ are preferably in the 6-position and/or 7-position of the tetralone system and in the 5-position and/or 6-position of the indanone system. They can be in the 5-position and/or 8-position of the tetralone system and in the 4-position and/or 7-position of the indanone system.

$R^1$ nd $R^2$ preferably each are H or methoxy or collectively are methylenedioxy. $R^1$ is preferably Br, $NO_2$, $NH_2$, methylamino, dimethylamino or acetamido and most preferably OH, ethoxy, F or Cl.

Ar is unsubstituted phenyl or phenyl substituted up to 5 times, that is, mono-, di-, tri-, tetra- or penta-substituted phenyl. Phenyl and mono-substituted phenyl are preferred.

Ar includes phenyl; o-, m- or p-fluorophenyl, o-, m- or p-chlorophenyl; o-, m- or p-trifluoromethylphenyl; o-, m- or p-tolyl; o-, m- or p-ethylphenyl; o-, m- or p-methoxyphenyl; o-, m- or p-ethoxyphenyl; o-, m- or p-bromophenyl; dimethoxyphenyl; and trifluoromethyl-chlorophenyl, e.g., 3-trifluoromethyl-4-chlorophenyl; 3,4,5-trimethoxyphenyl, 2,4,6-trimethylphenyl, 2,5-dimethoxy-4-chlorophenyl; 2,3,4,5-tetramethylphenyl, 3,6-dichloro-2,5-dimethoxyphenyl; 2,3,4,5,6-pentamethylphenyl.

Preferred Ar are phenyl, p-fluorophenyl, p-chlorophenyl and m-trifluoromethylphenyl.

The following compounds of Formula I, in which at least one of the substituents has one of the preferred structures given above, but which otherwise corresponds to Formula I, are preferred a. $R^1$ is H, OH, methoxy, ethoxy, F, Cl, Br, $NO_2$, $NH_2$, methylamino, dimethylamino or acetamido;
$R^2$ is H, OH, methoxy or ethoxy; or
$R^1$ and $R^2$ collectively are methylenedioxy;

b. $R^1$ is H, OH, methoxy, F or Cl;
$R^2$ is H, OH, methoxy; or
$R^1$ and $R^2$ collectively are methylenedioxy;

c. $R^1$ and $R^2$ each are H or methoxy or collectively are methylenedioxy;

d. $R^1$ and $R^2$ collectively are methylenedioxy;

e. $R^1$ is H, OH, methoxy, F or Cl and $R^2$ is H, OH or methoxy;

f. $R^1$ is $NO_2$;

g. $R^1$ is amino, methylamino, dimethylamino or acetamido;

h. $R^3$ is H, including those of (a)–(g);

i. $n$ is 2, including those of (a)–(g);

j. $n$ is 1, including those of (a)–(g);

k. Ar is phenyl, tolyl, fluorophenyl, chlorophenyl, trifluoromethylphenyl or trifluoromethylchlorophenyl; including those of (a)–(j);

l. Ar is phenyl, p-fluorophenyl, p-chlorophenyl or m-trifluoromethylphenyl; including those of (a)–(j);

m. $R^1$ and $R^2$ each are H or methoxy or collectively are methylenedioxy, and
Ar is phenyl, tolyl, fluorophenyl, chlorophenyl, trifluoromethylphenyl or trifluoromethylchlorophenyl, including those of (h)–(j);

n. $R^1$ and $R^2$ each are H or methoxy or collectively are methylenedioxy;
Ar is phenyl, p-fluorophenyl, p-chlorophenyl or m-trifluoromethylphenyl, and
$n$ is 2; and o. $R^1$ and $R^2$ each are H or methoxy or collectively are methylenedioxy,
$R^3$ is H,
Ar is phenyl and
$n$ is 2.

In Formula III, $R^4$ is preferably (H,$R^3$), most preferably (H,H). X is preferably Cl, Br or OH. In Formula V, $X^1$ is preferably carbonyl in the form of ketal or thioketal, for example, dimethyl ketal, diethyl ketal, ethylene ketal, trimethylene ketal, or dimethyl thioketal, diethyl thioketal, ethylene thioketal or trimethylene thioketal. $X^2$ is preferably OH, when $X^1$ is a functionally-modified carbonyl, or Br, if $X^1$ is free carbonyl.

In Formula VI, $R^7$ is preferably $-CH_2-C(=CH_2)-Ar$.

Preparation of compounds of Formula I is carried out by methods which are described in the literature, for example, in Houben-Weyl, Methoden der organischen Chemie (Methods of Organic Chemistry), Georg Thieme Verlag, Stuttgart; and Organic Reactions, John Wiley & Sons, Inc., New York), under known reaction conditions. Known variants of these reactions can also be used.

Most of the starting materials of FOrmulae II and VIII are known and can be prepared by methods reported in the literature. Phenylpiperidines of Formula II can be obtained by reacting 1-carbethoxy-4-piperidone or 1-benzyl-4-piperidone with organometallic compounds of the formula ArLi or ArMgBr and subsequently splitting off the blocking group by hydrolysis or hydrogenolysis.

Ketones of FOrmula III, $R^4$ is (H,$R^3$), can be obtained by cyclizing carboxylic acids of the formula $R^1R^2C_6H_3-(CH_2)_n-CHR^3-COOH$. The corresponding 2-hydroxymethyl compounds III, $R^4$ is $R^3$, $CH_2OH$, are obtained from the resulting ketone by reaction with formaldehyde. Mannich bases of Formulae III ($R^4$ is $R^3$, $CH_2NR^5R^6$), V ($X^1$ is CO) or VI are obtained by reacting the ketone with formaldehyde and an amine. Enaminoketones of Formula VII are obtained by reaction with formic acid esters and subsequent reaction with phenylpiperidines of Formula II.

Acids of Formula IV are obtained by reacting esters of the formula $R^1R^2C_6H_3-(CH_2)_{n+1}-COOAlkyl$ with ethyl formate to produce 2-hydroxymethylene derivatives of the formula $R^1R^2C_6H_3-(CH_2)_n-C(=CHOH)-COOAlkyl$ and reacting the latter with bases of Formula II to give the corresponding 2-(4-hydroxypiperidinomethylene) derivatives; these derivatives are hydrogenated and then saponified.

Ketone derivatives of Formula V ($X^1$ is functionally modified carbonyl) are made by reducing corresponding 1,2,3,4-tetrahydro-2-naphthoic acid 4-aryl-4-hydroxypiperidides. Amino-alcohols of Formula VIII are accessible by reacting corresponding 2-halogenomethyl-1-tetralols with bases of Formula II.

The starting materials can also be formed in situ and, without isolation, immediately converted to compounds of Formula I.

Tetralone and indanone derivatives of Formula I are preferably prepared from compounds of Formulae II, III ($R^4$ is $H,R^3$) and formaldehyde by the Mannich reaction.

Bases of Formula II can be used as free bases or as acid addition salts. Formaldehyde can be used in aqueous solution or dissolved in organic solvents, for example, lower alcohols, e.g., ethanol or isopropanol; or in gaseous form. Formaldehyde donors, e.g., paraformaldehyde, can be employed, preferably in alcoholic solution.

It is preferred to carry out the reaction in an inert solvent, for example, in an aqueous alcoholic solution or suspension, in which the ketone, aqueous formaldehyde solution and amino component are heated and acid is added. Suitable alcohols include methanol, ethanol and isopropanol. It is also possible to do the reaction under anhydrous conditions in an organic solvent. Suitable organic solvents include alcohols mentioned above as well as n-propanol, n-butanol, sec.-butanol, isobutanol, tert.-butanol, amyl alcohol, isoamyl alcohol, sec.-amyl alcohol and tert.-amyl alcohol; ethers, e.g., diethyl ether, diisopropyl ether, di-n-butyl ether, tetrahydrofuran (THF), dioxane, diglyme and 1,2-dimethoxyethane; amides, e.g., dimethylformamide (DMF); nitriles, e.g., acetonitrile; aromatic hydrocarbons, e.g., benzene, toluene and xylene; nitro compounds, e.g., nitrobenzene, and mixtures of solvents. Preferred mixtures include isopropanol/ diethyl ether and isopropanol/carbon tetrachloride. If ketone III is a liquid, the reaction can be done without a solvent in an excess of ketone.

If free amines II are reacted with ketones III, $R^4$ is ($H,R^3$), and formaldehyde or a formaldehyde donor, it is advantageous to add an acid to the reaction mixture. Organic and inorganic acids which can be employed for this purpose include hydrochloric acid, sulfuric acid, perchloric acid and acetic acid.

Reaction of amine II with formaldehyde and ketone III, $R^4$ is ($H,R^3$), can be carried out in one step. Also, formaldehyde can first be reacted with one of the two other components and the third added. That is, the hydroxymethyl compound is obtained from formaldehyde and amine II and the product reacted with the ketone before the Mannich condensation.

It is preferable to do the Mannich reaction at temperatures between about 0° and 140°, preferably between 20° and 85°. Reaction times are between 1 and 15 hours.

Compounds of Formula I can also be obtained by reacting a phenylpiperidine derivative of Formula II with a ketone of Formula III, $R^4$ is $CH_2$, ($R^3$, $CH_2X$) or ($R^3$, $CH_2NR^5R^6$). Suitable functional derivatives of these compounds can be used, for example, addition salts or quaternary ammonium salts of Mannich bases of Formula III, $R^4$ is ($R^3$, $CH_2NR^RR^6$). Reaction of these compounds is done as above, with or without a solvent, at temperatures between 0° and 140°. A base, for example, an alkali metal hydroxide, carbonate or alcoholate or a tertiary amine, can be added. If a ketone of Formula III, $R^4$ is ($R^3$, $CH_2X$), is used, an alkali metal iodide, such as potassium iodide, can also be added.

Compounds of Formula I can also be prepared from carboxylic acid derivatives of Formula IV by intramolecular cyclization. Acid IV can be reacted directly with a cyclizing agent, e.g., a protonic acid such as sulfuric acid or hydrogen fluoride, a Lewis acid, e.g., trifluoroacetic anhydride, tin-(IV) chloride, phosphorus pentachloride, in organic solvents such as benzene or toluene. Preferably, polyphosphoric acid is used at temperatures between 0° and 110°. A functional derivative of an acid IV, preferably an acid halide, for example, a chloride or bromide, can be treated with a Lewis acid to obtain a ketone I. The acid chlorides are accessible by reaction of acids IV with $SOCl_2$. Aluminum chloride has proven particularly suitable as a catalyst, as well as phosphorus-(V) chloride, phosphorus oxychloride and tin-(IV) chloride. The reaction is generally carried out in an inert organic solvent such as petroleum ether; hexane; carbon disulfide; a halogenated hydrocarbon, such as 1,2-dichloroethane; or nitrobenzene at temperatures between about −20° and +130° and reaction times of up to 4 hours.

Compounds of Formula I can also be obtained by solvolysis of corresponding compounds of Formula V in which the keto group and/or the hydroxyl group are present in a functionally-modified form. The keto group is preferably in the form of a ketal or thioketal, but it can be in the form of another ketone derivative, including a hemithioketal, for example, ethylene-, trimethylene-, dimethyl-or diethyl-hemithioketal; a phenylhydrazone; a semicarbazone; an oxime or a Girard derivative, for example, Girard T derivative.

The ketals are preferably split by treatment with acids. Examples of suitable acids include hydrochloric acid, sulfuric acid, perchloric acid, phosphoric acid, p-toluenesulfonic acid, formic acid, oxalic acid and Lewis acids, e.g., boron trifluoride etherate. Usually an inert solvent is used, for example, an alcohol, such as methanol or ethanol; an ether, such as dioxane; a ketone, such as acetone; or a carboxylic acid, such as acetic acid; and mixtures of these solvents with water. Acetic acid can serve simultaneously as a cleavage reagent and as a solvent. The thioketals are preferably cleaved by treatment with heavy metal compounds including mercury-(II) chloride, mercury-(II) oxide, cadmium carbonate and/or silver nitrate, preferably in aqueous alcohols. They can also be cleaved oxidatively, for example, with N-bromosuccinimide, bromine or thallium-(III) compounds, e.g., thallium tristrifluoroacetate. The remaining ketone derivatives are preferably cleaved in an acid medium. Reaction temperatures for the solvolysis are between about 0° and about 100°, preferably between 20° and 80°.

Compounds of formula V ($X^2$ is Cl, Br or I) are preferably obtained in situ from the corresponding 3,4-dehydropiperidine derivatives by addition of hydrogen halide. Halogen atoms bonded to a tertiary atom are easily split off with an acid or a base or by heating with water. Reaction temperatures are between about 0° and about 100°.

Compounds of Formula I can also be obtained by treating an aminoketone of Formula VI with formaldehyde, preferably in a slightly acid medium (pH about 2 to 3) at temperatures between about 20° and 100°, preferably 30° to 90°. Formaldehyde can be employed in this reaction in the forms used for the Mannich reaction described above, but, preferably is used as a 20–40% aqueous solution.

Compounds of Formula I can also be obtained by reducing enaminoketones of Formula VII, preferably by catalytic hydrogenation over a noble metal or nickel catalyst. Noble metals include platinum and palladium, which can be supported on charcoal, calcium carbonate or strontium carbonate, or in the form of oxides or of finely divided metal. Nickel is preferably used as Raney nickel. To avoid reduction of the keto group, it is preferable to hydrogenate under relatively mild conditions, for example, at pressures between 1 and 10 atmospheres and at relatively low temperatures, between 0° and 40°, preferably at room temperature. The hydrogenation is carried out in an inert solvent, for example, an alcohol, such as methanol, ethanol or isopropanol; a carboxylic acid, such as acetic acid; an ester, such as ethyl acetate, or an ether, such as THF or dioxane. Mixtures of solvents including mixtures with water can be used. An acid, e.g., hydrochloric acid, can be present.

Ketones of Formula I can also be prepared by oxidation of corresponding tetralol or indanol derivatives. Suitable oxidizing agents are those customarily used for oxidation of alcohols to ketones, for example, chromic acid (in aqueous acetone in the presence of sulfuric acid at about 0° to 80°), manganese-dioxide (in benzene, acetone or chloroform); dinitrogen tetroxide (in chloroform) or potassium permanganate (in acetone at room temperature). Alcohols of Formula VIII can also be oxidized by the Oppenauer method. An excess of a ketone such as acetone, butanone or cyclohexanone is used, in the presence of an aluminum alcoholate, such as aluminum isopropylate, in an inert solvent, such as benzene, toluene or dioxane, at temperatures between about 60° and 110°.

In compounds of Formula I, $R^1$, $R^2$ and/or Ar can be converted into one or more other $R^1$, $R^2$ and/or Ar by reduction, alkylation or acylation and/or by diazotization and subsequent treatment with a halogen compound or a solvolyzing agent.

Nitro groups can be reduced to amino groups by catalytic hydrogenation under mild conditions indicated in greater detail above or chemically, for example, with iron powder or iron (II) salts, such as iron-(II) sulfate, in an aqueous medium at temperatures between 50° and 100°, or with sodium sulfide or sodium dithionite in an aqueous or alcoholic medium.

Hydroxyl groups can be alkylated to alkoxy or cycloalkoxy and/or amino to monoalkylamino or dialkylamino groups by reaction with corresponding alkyl or cycloalkyl halides, including methyl chloride, methyl bromide, methyl iodide, cyclopentyl, cyclohexyl chloride, bromide or iodide, alkyl or cycloalkyl sulfates, such as dimethyl sulfate; and alkyl or cycloalkyl p-toluenesulfonates, such as methyl p-toluenesulfonate. It is preferable to add a base such as potassium carbonate or sodium bicarbonate in an inert organic solvent, such as methanol or acetone, to the reaction mixture.

Alkylation using diazoalkanes, such as diazomethane, preferably in ether or dioxane, is done at temperatures between 0° and 100°.

Hydroxy or amino groups can be acylated to give acyloxy or acylamino groups, respectively, by reaction with an acid halide, such as acetyl chloride, or an acid anhydride, such as acetic anhydride. A base such as sodium carbonate or potassium carbonate or a tertiary amine, such as pyridine or triethylamine is usually used, preferably in an inert solvent such as benzene. Acylation temperatures are between 0° and 100°.

Halogen-containing compounds of Formula I can be obtained from the corresponding amino compounds, buy diazotization, using salts or esters of nitrous acid, e.g., $NaNO_2$ or n-butyl nitrite, in aqueous hydrochloric acid at temperatures between about −20° and +10°, and conversion of the resulting diazonium salt to the halogen compound. Fluorine compounds (I, $R^1$ is F) are preferably obtained by reacting the corresponding diazonium compound with $HBF_4$ or $NH_4BF_4$ to give the diazonium tetrafluoborate and subsequently decomposing this at about 100° to 200° with or without an inert solvent, such as toluene, xylene, 1,2,4-trichlorobenzene or dioxane.

If diazotization is carried out with $NaNO_2$ in anhydrous hydrofluoric acid, the fluorine compound is obtained directly by heating. It is preferable to replace the diazonium group by chlorine or bromine using $Cu_2Cl_2$ or $Cu_2Br_2$ in a hot, aqueous solution. The diazonium compounds are heated in an aqueous acid medium to obtain the corresponding hydroxy compounds by elimination of nitrogen.

Compounds of Formula I can be converted into physiologically acceptable acid addition salts by treatment with acids. Inorganic or organic acids can be used including aliphatic, alicyclic, araliphatic, aromatic, heterocyclic, monobasic or polybasic carboxylic and sulfonic acids. The following are exemplary: mineral acids, such as hydrochloric acid, hydrobromic acid, hydriodic acid, sulfuric acid, nitric acid and phosphoric acids, such as orthophosphoric acid; organic acids, such as formic acid, acetic acid, propionic acid, butyric acid, pivalic acid, diethylacetic acid, malonic acid, succinic acid, pimelic acid, fumaric acid, maleic acid, citric acid, gluconic acid, tartaric acid, malic acid, benzoic acid, salicylic acid, 2-phenylpropionic acid, ascorbic acid, nicotinic acid, isonicotinic acid; and sulfonic acids including methanesulfonic or ethanesulfonic acid, ethanedisulfonic acid, 2-hydroxyethanesulfonic acid, benzensulfonic, p-toluene-sulfonic acid and naphthalenemonosulfonic and naphthalanedisulfonic acids.

Free bases of Formula I can be liberated from their acid addition salts by treatment with a base, e.g., sodium hydroxide, potassium hydroxide, sodium carbonate or potassium carbonate.

Compounds of Formula I possess a center of asymmetry and are obtained in the snythesis as racemates. If optically active starting materials are used, they are obtained in an optically active form. Racemates can be resolved by mechanical or chemical means into their optical antipodes by known methods. It is preferable to form diastereomers from the racemate by reaction with an optically-active resolving agent. Examples of suitable resolving agents are optically active acids, such as tartaric acid, dibenzoyltartaric acid, daicetyltartaric acid, camphorsulfonic acids, mandelic acid, malic acid and lactic acid.

Compounds of Formula I are well tolerated and have valuable pharmacological properties. They are central nervous system depressants, with calming, sedating, tranquilizing, neuroleptic and/or anti-depressive activity. The substances are effective in the avoidance-inhibition test of Mueller-Calgan et al., Arch. Pharmacol. Exptl. Pathol., volume 260, 1968, pages 178–179. The other effects are determined by customary methods, as on mice, rats, dogs and Rhesus monkeys. The substances have an anti-emetic effect against vomiting induced by apomorphine in beagle dogs. Bactericidal and fungicidal activity against Gram-positive and Gram-negative bacteria and Pseudomonas are observed.

The compounds can be used as medicaments and as intermediate products for the preparation of other medicaments.

The new compounds can be mixed with solid, liquid and/or semi-liquid medicinal excipients and used as medicaments in human or veterinary medicine. Suitable excipients include organic or inorganic materials which are suitable for parenteral or enteral administration or topical application and which do not react with the new compounds, for example, water, vegetable oils, benzyl alcohols, polyethylene glycols, gelatine, lactose, starch, magnesium stearate, talc, petroleum jelly or cholesterol. Solutions, preferably oily or aqueous solutions, as well as suspensions, emulsions or implants are used for parenteral administration. The new compounds can also be lyophilized and the resulting lyophilizates can be used, for example, for the production of preparations for injection. Tablets, dragees, capsules, syrups, elixirs or suppositories, for example, are suitable for enteral administration, and ointments, creams or powders are suitable for topical use. The preparations can be sterilized and/or treated with auxiliary substances, including lubricants, preservatives, stabilizers and/or wetting agents, emulsifiers, salts for controlling osmotic pressure, buffers, dyestuffs, flavorings and/or perfumes. The formulations can also contain one or more other active compounds, for example, vitamins.

Compounds of this invention are preferably administered in dosages between about 0.1 and 100, in particular 0.5 and 20, mg. per dosage unit. The daily dosage is preferably between about 0.002 and 2 mg./kg. of body weight. Oral administration is preferred.

In this regard, the compounds of this invention can be administered like the known compounds 4-[3-(2-chlorophenothiazin-10-yl)-propyl]-1-piperazineethanol and 2-chloro-10-(3-dimethylaminopropyl)-phenothiazine.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

Compounds of Formula I mentioned in the Examples which follow are particularly suitable for the production of pharmaceutical preparations.

In the following text "customary working up" means: the reaction mixture is treated with aqueous potassium carbonate solution and chloroform or ether and is shaken, the phases are separated and the aqueous phase is washed with water, dried over sodium sulfate and evaporated. The crude base obtained is purified via the hydrochloride.

EXAMPLE 1 a. 21.35 g. of 4-phenylpiperidin-4-ol hydrochloride, 14.6 g. of 1-tetralone and 10 ml. of 37% formaldehyde solution in 50 ml. of ethanol are heated under reflux for 1 hour. The mixture is evaporated and ether is added to the residue, after which the phases are separated by decantation to give 2-(4-phenyl-4-hydroxypiperidinomethyl)-1-tetralone hydrochloride; m.p. 164°–167°.

The following are obtained analogously from 4-phenylpiperidin-4-ol hydrochloride, formaldehyde, and 5-, 6-, 7- or 8-hydroxy-1-tetralone, 6,7-dihydroxy-1-tetralone, 5-, 6-, 7- or 8-methoxytetralone, 6-n-butoxytetralone, 6-cyclopropyloxytetralone, 6-cyclopentyloxytetralone, 6-cyclohexyloxytetralone, 6,7-dimethoxytetralone, 5-, 6-, 7- or 8-fluorotetralone, 5-, 6-, 7- or 8-chlorotetralone, 5-, 6-, 7- or 8-bromotetralone, 5-, 6-, 7- or 8-aminotetralone, 5-, 6-, 7- or 8-methylaminotetralone, 6-n-butylaminotetralone, 5-, 6-, 7- or 8-dimethylaminotetralone, 6-di-n-butylaminotetralone, 6-formyloxytetralone, 5-, 6-, 7-or 8-acetoxytetralone, 6-propionyloxytetralone, 6-butyryloxytetralone, 6-trimethylacetoxytetralone, 6-tert.-butylacetoxytetralone, 5-, 6-, 7- or 8-acetamidotetralone, 6-butyramidotetralone or 6,7-methylenedioxy-1-tetralone, respectively:

2(4-Phenyl-4-hydroxypiperidinomethyl)-5-hydroxy-1-tetralone;

2-(4-Phenyl-4-hydroxypiperidinomethyl)-6-hydroxy-1-tetralone, m.p. 187°–189°;

2-(4-Phenyl-4-hydroxypiperidinomethyl)-7-hydroxy-1-tetralone;

2-(4-Phenyl-4-hydroxypiperidinomethyl)-8-hydroxy-1-tetralone;

2-(4-Phenyl-4-hydroxypiperidinomethyl)-6,7-dihydroxy-1-tetralone;

2-(4-Phenyl-4-hydroxypiperidinomethyl)-5-methoxy-1-tetralone;

2-(4-Phenyl-4-hydroxypiperidinomethyl)-6-methoxy-1-tetralone, m.p. 163°–165°;

2-(4-Phenyl-4-hydroxypiperidinomethyl)-7-methoxy-1-tetralone;

2-(4-Phenyl-4-hydroxypiperidinomethyl)-8-methoxy-1-tetralone;

2-(4-Phenyl-4-hydroxypiperidinomethyl)-6-n-butoxy-1-tetralone;

2-(4-Phenyl-4-hydroxypiperidinomethyl)-6-cyclopropyloxy-1-tetralone;

2-(4-Phenyl-4-hydroxypiperidinomethyl)-6-cyclopentyloxy-1-tetralone, hydrochloride, m.p. 187°–189°;

2-(4-Phenyl-4-hydroxypiperidinomethyl)-6-cyclohexyloxy-1-tetralone;

2-(4-Phenyl-4-hydroxypiperidinomethyl)-6,7-dimethoxy-1-tetralone, hydrochloride, m.p. 175°–177°;

2-(4-Phenyl-4-hydroxypiperidinomethy)-5-fluoro-1-tetralone;

2-(4-Phenyl-4-hydroxypiperidinomethyl)-6-fluoro-1-tetralone;

2-(4-Phenyl-4-hydroxypiperidinomethyl)-7-fluoro-1-tetralone;

2-(4-Phenyl-4-hydroxypiperidinomethyl)-8-fluoro-1-tetralone;

2-(4-Phenyl-4-hydroxypiperidinomethyl)-5-chloro-1-tetralone;

2-(4-Phenyl-4-hydroxypiperidinomethyl)-6-chloro-1-tetralone;

2-(4-Phenyl-4-hydroxypiperidinomethyl)-7-chloro-1-tetralone;

2-(4-Phenyl-4-hydroxypiperidinomethyl)-8-chloro-1-tetralone;

2-(4-Phenyl-4-hydroxypiperidinomethyl)-5-bromo-1-tetralone;

2-(4-Phenyl-4-hydroxypiperidinomethyl)-6-bromo-1-tetralone;

2-(4-Phenyl-4-hydroxypiperidinomethyl)-7-bromo-1-tetralone;
2-(4-Phenyl-4-hydroxypiperidinomethyl)-8-bromo-1-tetralone;
2-(4-hydroxypiperidinomethyl)-5-amino-1-tetralone;
2-(4-Phenyl-4-hydroxypiperidinomethyl)-6-amino-1-tetralone;
2-(4-Phenyl-4-hydroxypiperidinomethyl)-7-amino-1-tetralone;
2-(4-Phenyl-4-hydroxypiperidinomethyl)-8-amino-1-tetralone;
2-(4-Phenyl-4-hydroxypiperidinomethyl)-5-methylamino-1-tetralone;
2-(4-Phenyl-4-hydroxypiperidinomethyl)-6-methylamino-1-tetralone;
2-(4-Phenyl-4-hydroxypiperidinomethyl)-7-methylamino-1-tetralone;
2-(4-Phenyl-4-hydroxypiperidinomethyl)-8-methylamino-1-tetralone;
2-(4-Phenyl-4-hydroxypiperidinomethyl)-6-n-butylamino-1-tetralone;
2-(4-Phenyl-4-hydroxypiperidinomethyl)-5-dimethylamino-1-tetralone;
2-(4-Phenyl-4-hydroxypiperidinomethyl)-6-dimethylamino-1-tetralone;
2-(4-Phenyl-4-hydroxypiperidinomethyl)-7-dimethylamino-1-tetralone;
2-(4-Phenyl-4-hydroxypiperidinomethyl)-8-dimethylamino-1-tetralone;
2-(4-Phenyl-4-hydroxypiperidinomethyl)-6-di-n-butylamino-1-tetralone;
2-(4-Phenyl-4-hydroypiperidinomethyl)-6-formyloxy-1-tetralone;
2-(4-Phenyl-4-hydroxypiperidinomethyl)-5-acetoxy-1-tetralone;
2-(4-Phenyl-4-hydroxypiperidinomethyl)-6-acetoxy-1-tetralone;
2-(4-Phenyl-4-hydroxypiperidinomethyl)-7-acetoxy-1-tetralone;
2-(4-Phenyl-4-hydroxypiperidinomethyl)-8-acetoxy-1-tetralone;
2-(4-Phenyl-4-hydroxypiperidinomethyl)-6-propionyloxy-1-tetralone, hydrochloride, m.p. 170°–172°;
2-(4-phenyl-4-hydroxypiperidinomethyl)-6-butyryloxy-1-tetralone;
2-(4-Phenyl-4-hydroxypiperidinomethyl)-6-trimethylacetoxy-1-tetralone;
2-(4-Phenyl-4-hydroxypiperidinomethyl)-6-tert.-butylacetoxy-1-tetralone;
2-(4-Phenyl-4-hydroxypiperidinomethyl)-5-acetamido-1-tetralone;
2-(4-Phenyl-4-hydroxypiperidinomethyl)-6-acetamido-1-tetralone;
2-(4-Phenyl-4-hydroxypiperidinomethyl)-7-acetamido-1-tetralone;
2-(4-Phenyl-4-hydroxypiperidinomethyl)-8-acetamido-1-tetralone;
2-(4-Phenyl-4-hydroxypiperidinomethyl)-6-butyramido-1-tetralone;
2-(4-Phenyl-4-hydroxypiperidinomethyl)-6,7-methylene-dioxy-1-tetralone, hydrochloride, m.p. 196°–198°.

b. 3.51 g. of 2-(4-phenyl-4-hydroxypiperidinomethyl)-6-hydroxy-1-tetralone are dissolved in a mixture of 45 ml. of methanol and 5 ml. of water. An ethereal solution of diazomethane is added at 20° until a faint yellow coloration remains. The mixture is evaporated to give 2-(4-phenyl-4-hydroxypiperidino-methyl)-6-methoxy-1-tetralone, m.p. 163°–165°.

c. A mixture of 1 g. of 2-(4-phenyl-4-hydroxypiperidinomethyl)-6-hydroxy-1-tetralone and 10 ml. of propionic anhydride is kept at 20° for 24 hours and poured on ice. 2-(4-phenyl-4-hydroxypiperidinomethyl)-6-propionyloxy-1-tetralone is obtained, hydrochloride, m.p. 170°–172°.

EXAMPLE 2

A mixture of 21.35 g. of 4-phenylpiperidin-4-ol hydrochloride, 20.6 g. of 6,7-dimethoxy-1-tetralone and 8 g. of paraformaldehyde in 200 ml. of ethanol (or isopropanol) is heated under reflux for 4 hours. The solvent is evaporated and the residue is made into a slurry with acetone/ether and is filtered off. 2-(4-phenyl-4-hydroxypiperidinomethyl)-6,7-dimethoxy-1-tetralone hydrochloride, m.p. 175°–177°, is obtained.

The following are obtained by reaction with the corresponding tetralones and paraformaldehyde, from the hydrochlorides of 4-o-tolylpiperidin-4-ol, 4-m-tolylpiperidin-4-ol, 4-p-tolylpiperidin-4-ol, 4-p-ethylphenyl-piperidin-4-ol, 4-p-isopropylphenyl-piperidin-4-ol, 4-p-n-butylphenylpiperidin-4-ol, 4-o-methoxyphenyl-piperidin-4-ol, 4-m-methoxyphenyl-piperidin-4-ol, 4-p-methoxyphenyl-piperidin-4-ol, 4-o-fluorophenylpiperidin-4-ol, 4-m-fluorophenylpiperidin-4-ol, 4-p-fluorophenylpiperidin-4-ol, 4-o-chlorophenylpiperidin-4-ol, 4-m-chlorophenylpiperidin-4-ol, 4-p-chlorophenyl-piperidin-4-ol, 4-o-bromophenylpiperidin-4-ol, 4-m-bromophenylpiperidin-4-ol, 4-p-bromophenylpiperidin-4-ol, 4-o-trifluoromethylphenylpiperidin-4-ol, 4-m-trifluoromethyl-phenylpiperidin-4-ol or 4-p-trifluoromethylphenylpiperidin-4-ol:

2-(4-o-Tolyl-4-hydroxypiperidinomethyl)-1-tetralone;
2-(4-o-Tolyl-4-hydroxypiperidinomethyl)-6,7-dimethoxy-1-tetralone;
2-(4-o-Toly-4-hydroxypiperidinomethyl)-6,7-methylene-dioxy-1-tetralone;
2-(4-m-tolyl-4-hydroxypiperidinomethyl)-1-tetralone;
2-(4-m-Tolyl-4-hydroxypiperidinomethyl)-6,7-dimethoxy-1-tetralone, hydrochloride, m.p. 157°–159°;
2-(4-m-Tolyl-4-hydroxypiperidinomethyl)-6,7-methylene-dioxy-1-tetralone;
2-(4-p-Tolyl-4-hydroxypiperidinomethyl)-1-tetralone;
2-(4-p-Tolyl-4-hydroxypiperidinomethyl)-6,7-dimethyoxy-1-tetralone;
2-(4-p-Tolyl-4-hydroxypiperidinomethyl)-6,7-methylene-dioxy-1-tetralone;
2-(4-p-Ethylphenyl-4-hydroxypiperidinomethyl)-1-tetralone;
2-(4-p-Isopropylphenyl-4-hydroxypiperidinomethyl)-1-tetralone;
2-(4-n-Butylphenyl-4-hydroxypiperidinomethyl)-1-tetralone;
2-(4-o-Methoxyphenyl-4-hydroxypiperidinomethyl)-1-tetralone;
2-(4-o-Methoxyphenyl-4-hydroxypiperidinomethyl)-6,7-dimethoxy-1-tetralone;
2-(4-o-Methoxyphenyl-4-hydroxypiperidinomethyl)-6,7-methylenedioxy-1-tetralone;
2-(4-m-Methoxyphenyl-4-hydroxypiperidinomethyl)-1-tetralone;
2-(4-m-Methoxyphenyl-4-hydroxypiperidinomethyl)-6,7-dimethoxy-1-tetralone;

2-(4-m-Methoxyphenyl-4-hydroxypiperidinomethyl)-6,7-methylenedioxy-1-tetralone;
2-(4-p-Methoxyphenyl-4-hydroxypiperidinomethyl)-1-tetralone;
2-(4-p-Methoxyphenyl-4-hydroxypiperidinomethyl)-6,7-dimethoxy-1-tetralone;
2-(4-p-Methoxyphenyl-4-hydroxypipieridinomethyl)-6,7-methylenedioxy-1-tetralone;
2-(4-o-Fluorophenyl-4-hydroxypiperidinomethyl)-1-tetralone;
2-(4-o-Fluorophenyl-4-hydroxypiperidinomethyl)-6,7-dimethoxy-1-tetralone;
2-(4-o-Fluorophenyl-4-hydroxypiperidinomethyl)-6,7-methylenedioxy-1-tetralone;
2-(4-m-Fluorophenyl-4-hydroxypiperidinomethyl)-1-tetralone;
2-(4-m-Fluorophenyl-4-hydroxypiperidinomethyl)-6,7-dimethoxy-1-tetralone;
2-(4-m-Fluorophenyl-4-hydroxypiperidinomethyl)-6,7-methylenedioxy-1-tetralone;
2-(4-p-Fluorophenyl-4-hydroxypiperidinomethyl)-1-tetralone;
2-(4-p-Fluorophenyl-4-hydroxypiperidinomethyl)-6-methoxy-1-tetralone;
2-(4-p-Fluorophenyl-4-hydroxypiperidinomethyl)-7-methoxy-1-tetralone;
2-(4-p-Fluorophenyl-4-hydroxypiperidinomethyl)-6,7-dimethoxy-1-tetralone, hydrochloride, m.p. 193°–195°;
2-(4-p-Fluorophenyl-4-hydroxypiperidinomethyl)-6,7-methylenedioxy-1-tetralone;
2-(4-o-Chlorophenyl-4-hydroxypiperidinomethyl)-1-tetralone;
2-(4-o-Chlorophenyl-4-hydroxypiperidinomethyl)6,7-dimethoxy-1-tetralone;
2-(4-o-Chlorophenyl-4-hydroxypiperidinomethyl)-6,7-methylenedioxy-1-tetralone;
2-(4-m-Chlorophenyl-4-hydroxypiperidinomethyl)-1-tetralone;
2-(4-m-Chlorophenyl-4-hydroxypiperidinomethyl)-6,7-dimethoxy-1-tetralone;
2-(4-m-chlorophenyl-4-hydroxypiperidinomethyl)-6,7-methylenedioxy-1-tetralone;
2-(4-p-Chlorophenyl-4-hydroxypiperidinomethyl)-1-tetralone;
2-(4-p-Chlorophenyl-4-hydroxypiperidinomethyl)-6,7-dimethoxy-1-tetralone, hydrochloride, m.p. 227°–228°;
2-(4-p-chlorophenyl-4-hydroxypiperidinomethyl)-6,7-methylenedioxy-1-tetralone;
2-(4-p-Chlorophenyl-4-hydroxypiperidinomethyl-7-chloro-1-tetralone;
2-(4-o-Bromophenyl-4-hydroxypiperidinomethyl)-1-tetralone;
2-(4-o-Bromophenyl-4-hydroxypiperidinomethyl)-6,7-dimethoxy-1-tetralone;
2-(4o-Bromophenyl-4-hydroxypiperidinomethyl)-6,7-methylenedioxy-1-tetralone;
2-(4-m-Bromophenyl-4-hydroxypiperidinomethyl)-1-tetralone;
2-(4-m-Bromophenyl-4-hydroxypiperidinomethyl)-6,7-dimethoxy-1-tetralone;
2-(4-m-Bromophenyl-4-hydroxypiperidinomethyl)-6,7-methylenedioxy-1-tetralone;
2-(4-p-Bromophenyl-4-hydroxypiperidinomethyl)-1-tetralone;
2-(4-p-Bromophenyl-4-hydroxypiperidinomethyl-6,7-dimethoxy-1-tetralone;
2-(4-p-Bromophenyl-4-hydroxypiperidinomethyl)-6,7-methylenedioxy-1-tetralone;
2-(4-o-Trifluoromethylphenyl-4-hydroxypiperidinomethyl)-1-tetralone;
2-(4-o-Trifluoromethylphenyl-4-hydroxypiperidinomethyl)-6,7-dimethoxy-1-tetralone;
2-(4-o-trifluoromethylphenyl-4-hydroxypiperidinomethyl)-6,7-methylenedioxy-1-tetralone;
2-(4-m-Trifluoromethylphenyl-4-hydroxypiperidinomethyl)-1-tetralone;
2-(4-m-Trifluoromethylphenyl-4-hydroxypiperidinomethyl)-6,7-dimethoxy-1-tetralone, hydrochloride, m.p. 212°–214°;
2-(4-m-Trifluoromethylphenyl-4-hydroxypiperidinomethyl)-6,7-methylenedioxy-1-tetralone;
2-(4-p-Trifluoromethylphenyl-4-hydroxypiperidinomethyl)-1-tetralone;
2-(4-p-Trifluoromethylphenyl-4-hydroxypiperidinomethyl)-6,7-dimethoxy-1-tetralone;
2-(4-p-Trifluoromethylphenyl-4-hydroxypiperidinomethyl)-6,7-methylenedioxy-1-tetralone; and
2-[4-(3-Trifluoromethyl-4-chlorophenyl)-4-hydroxypiperidinomethyl]-6,7-dimethoxy-1-tetralone, hydrochloride, m.p. 199°–202°.

EXAMPLE 3

2-(4-Phenyl-4-hydroxypiperidinomethyl)-5,6-dimethoxy-1-indanone hydrochloride, m.p. 205°–207°, is obtained following Example 2 from 4-phenylpiperidin-4-ol, 5,6-dimethoxyindanone and formaldehyde, after a reaction period of 20 hours.

The following are obtained analogously:

2-(4-Phenyl-4-hydroxypiperidinomethyl)-1-indanone;
2-(4-Phenyl-4-hydroxypiperidinomethyl)-5-methoxy-1-indanone;
2-(4-Phenyl-4-hydroxypiperidinomethyl)-6-methoxy-1-indanone;
2-(4-Phenyl-4-hydroxypiperidinomethyl)-5,6-methylenedioxy-1-indanone;
2-(4-p-Fluorophenyl-4-hydroxypiperidinomethyl)-1-indanone;
2-(4-p-Fluorophenyl- 4-hydroxypiperidinomethyl)-5-methoxy-1-indanone;
2-(4-p-Fluorophenyl-4-hydroxypiperidinomethyl)-6-methoxy-1-indanone;
2-(4-p-Fluorophenyl-4-hydroxypiperidinomethyl)-5,6-dimethoxyl-1-indanone;
2-(4-p-Fluorophenyl-4-hydroxypiperidinomethyl)-5,6-methylenedioxy-1-indanone;
2-(4-m-Trifluoromethylphenyl-4-hydroxypiperidinomethyl)-1-indanone;
2-(4-m-Trifluoromethylphenyl-4-hydroxypiperidinomethyl)-5-methoxy-1-indanone;
2-(4-m-Trifluoromethylphenyl-4-hydroxypiperidinomethyl)-6-methoxy-1-indanone;
2-(4-m-Trifluoromethylphenyl-4-hydroxypiperidinomethyl)-5,6-dimethoxy-1-indanone; and
2-(4-m-Trifluoromethylphenyl-4-hydroxypiperidinomethyl)-5,6-methylenedioxy-1-indanone.

EXAMPLE 4 a. A mixture of 19.1 g. of 7-nitro-1-tetralone, 21.35 g. of 4-phenylpiperidin-4-hydrochloride, 10 ml. of 37% formaldehyde solution and 1 l. of 1,2-dimethoxyethane is heated under reflux for 30 hours. The mixture is evaporated and worked up according to Example 1 to give 2-(4-phenyl-4-hydroxypiperidinomethyl-7-nitro-1-tetralone.

The following are obtained in the same way:

2-(4-Phenyl-4-hydroxypiperidinomethyl)-5-nitro-1-tetralone;
2-(4-Phenyl-4-hydroxypiperidinomethyl)-6-nitro-1-tetralone;
2-(4-Phenyl-4-hydroxypiperidinomethyl)-8-nitro-1-tetralone;
2-(4-p-Fluorophenyl-4-hydroxypiperidinomethyl)-7-nitro-1-tetralone;
2-(4-m-Trifluoromethylphenyl-4-hydroxypiperidinomethyl)-7-nitro-1-tetralone.

b. 4.15 g. of 2-(4-phenyl-4-hydroxypiperidinomethyl)-7-nitro-1-tetralone hydrochloride are dissolved in 30 ml. of methanol and are reduced at 20° and 1 atmosphere over 0.3 g. of pre-reduced platinum oxide. After the calculated quantity of hydrogen has been absorbed, the mixture is filtered, evaporated and worked up in the customary manner to give 2-(4-phenyl-4-hydroxypiperidinomethyl)-7-amino-1-tetralone.

c. A mixture of 4.17 g. of 2-(4-phenyl-4-hydroxypiperidinomethyl)-6-nitro-1-tetralone hydrochloride, 20 g. of iron-(II) sulfate heptahydrate, 45 ml. of water and 0.15 ml. of concentrated hydrochloric acid is heated at 100° with stirring. 10 ml. of concentrated ammonium hydroxide solution are added at 80° and the mixture is heated for 10 minutes more on a steam bath. It is allowed to cool, extracted with chloroform and worked up to give 2-(4-phenyl-4-hydroxypiperidinomethyl)-6-amino-1-tetralone.

d. 3.5 g. of 2-(4-phenyl-4-hydroxypiperidinomethyl)-6-amino-1-tetralone are dissolved in 100 ml. of benzene. 5.3 g. of sodium carbonate are added and the mixture is cooled to 10° while a solution of 0.75 g. of acetyl chloride in 50 ml. of benzene is added dropwise at 10° with stirring. The mixture is stirred for 30 minutes. 5.3 g. more of sodium carbonate are added and the mixture is stirred for 3 hours more at 20°. It is then heated under reflux for 10 minutes, filtered and worked up in the customary manner. 2-(4-Phenyl-4-hydroxypiperidinomethyl)-6-acetamido-1-tetralone is obtained.

e. 3.5 g. of 2-(4-phenyl-4-hydroxypiperidinomethyl)-6-amino-1-tetralone are dissolved in 20 ml. of 2 N hydrochloric acid and 0.7 g. of NaNO$_2$ are added at 0°. A solution of 1.4 g. of NH$_4$BF$_4$ in 5 ml. of water is then added with stirring. The mixture is stirred for 20 minutes more. The resulting precipitate is filtered off, washed with a little ice cold 5% NH$_4$BF$_4$ solution and a little methanol and ether and is suspended in 75 ml. of 1,2,4-trichlorobenzene containing 5 g. of NaF. The solution is heated at 140° for 30 minutes and is evaporated and the residue is worked up in the customary manner. 2-(4-Phenyl-4-hydroxypiperidinomethyl)-6-fluoro-1-tetralone is obtained.

f. A solution of 0.7 g. of NaNO$_2$ in 3 ml. of water is added dropwise to a stirred solution of 3.5 g. of 2-(4-phenyl-4-hydroxypiperidinomethyl)-6-amino-1-tetralone in 10 ml. of 4 N hydrochloric acid. The mixture is warmed until nitrogen evolution has ceased. It is cooled, neutralized with potassium carbonate and worked up with chloroform in the customary manner. 2-(4-Phenyl-4-hydroxypiperdinomethyl)-6-hydroxy-1-tetralone is obtained. EXAMPLE 5

The following are obtained from 2-methyl-1-tetralone or further substituted 2-methyl-1-tetralones following Example 1 but heating under reflux for 12 hours:

2-(4-Phenyl-4-hydroxypiperidinomethyl)-2-methyl-1-tetralone;
2-(4-Phenyl-4-hydroxypiperidinomethyl)-2-methyl-6-methoxy-1-tetralone;
2-(4-Phenyl-4-hydroxypiperidinomethyl)-2-methyl-7-methoxy-1-tetralone;
2-(4-Phenyl-4-hydroxypiperidinomethyl)-2-methyl-6,7-dimethoxy-1-tetralone;
2-(4-Phenyl-4-hydroxypiperidinomethyl)-2-methyl-6,7-methylenedioxy-1-tetralone;
2-(4-p-Fluorophenyl-4-hydroxypiperidinomethyl)-2-methyl-1-tetralone;
2-(4-p-Fluorophenyl-4-hydroxypiperidinomethyl)-2-methyl-6-methoxy-1-tetralone;
2-(4-p-Fluorophenyl-4-hydroxypiperidinomethyl)-2-methyl-7-methoxy-1-tetralone;
2-(4-p-Fluorophenyl-4-hydroxypyperidinomethyl)-2-methyl-6,7-dimethoxy-1-tetralone;
2-(4-p-Fluorophenyl-4-hydroxypyperidinomethyl)-2-methyl-6,7-methylenedioxy-1-tetralone;
2-(4-m-Trifluoromethylphenyl-4-hydroxypiperidinomethyl)-2-methyl-1-tetralone;
2-(4-m-Trifluorometthylphenyl-4-hydroxypiperidinomethyl)-2-methyl-6-methoxy-1-tetralone;
2-(4-m-Trifluoromethylphenyl-4-hydroxypiperidinomethyl)-2-methyl-7-methoxy-1-tetralone;
2-(4-m-Trifluoromethylphenyl-4-hydroxypiperidinomethyl)-2-methyl-6,7-dimethoxy-1-tetralone; and
2-(4-m-Trifluoromethylphenyl-4-hydroxypiperidinomethyl)-2-methyl-6,7-methylenedioxy-1-tetralone.

EXAMPLE 6

5 drops of 2 N sodium hydroxide solution are added to a solution of 15.8 g. of 2-methylene-1-tetralone and 17.7 g. of 4-phenylpiperidin-4-ol in 150 ml. of ethanol and the mixture is allowed to stand for 2 hours at 20°. After evaporation, the residue is taken up in dilute hydrochloric acid and washed with ether. The aqueous phase is worked up in the customary manner to give 2-(4-phenyl-4-hydroxypiperidinomethyl)-1-tetralone, hydrochloride, m.p. 164°–167°.

EXAMPLE 7

1.95 g. of 2-chloromethyl-1-tetralone, prepared by reaction of phosphorus trichloride and 2-hydroxymethyl-1-tetralone, 3.54 g. of 4-phenylpiperidin-1-ol and 1 g. of potassium carbonate in 20 ml. of isopropanol are heated under reflux for 3 hours. The mixture is evaporated and worked up with water and ether to give 2-(4-phenyl-4-hydroxypiperidinomethyl)-1-tetralone. Hydrochloride, M.P. 164°–167°.

EXAMPLE 8

2 g. of 4-p-chlorophenylpiperidin-4-ol are dissolved in 30 ml. of DMF. 4.05 g. of 2-dimethylaminomethyl-6,7-dimethoxy-1-tetralone methiodide, obtainable by reacting 6,7-dimethoxy-1-tetralone with dimethylamine and formaldehyde and quaternizing the product with CH$_3$I, and 1 g. of Na$_2$CO$_3$ are added and the mixture is stirred for 4 hours at 20° under N$_2$. After the customary work up, 2-(4-p-chlorophenyl-4-hydroxypiperidinomethyl-6,7-dimethoxy-1-tetralone is obtained. Hydrochloride, m.p. 227°–228°.

EXAMPLE 9

4.13 g. of 4-(3,4-dimethoxyphenyl)-2-(4-phenyl-4-hydroxypiperidinomethyl)-butyric acid, prepared by condensing ethyl 4-(3,4-dimethoxyphenyl)-butyrate with ethyl formate to give a 2-hydroxymethylene derivative, reacting this with 4-phenylpiperidin-4-ol to give ethyl 2-(4-hydroxypiperidinomethylene)-4-(3,4-dimethoxyphenyl)-butyrate, hydrogenating and saponifying, in 50 g. of polyphosphoric acid are stirred for 2 hours at 70°–80°. The reaction mixture is poured onto ice. After the customary work up, 2-(4-phenyl-4-hydroxypiperidinomethyl)-6,7-dimethoxy-1-tetralone is obtained; hydrochloride, m.p. 175°–177°.

EXAMPLE 10

4.39 g. of 1,1-ethylenedioxy-2-(4-phenyl-4-hydroxypiperidinomethyl)-6,7-dimethoxytetralin, obtainable by reducing 1,1-ethylenedioxy-6,7-dimethoxy-1,2,3,4-tetrahydro-2-naphthoic acid 4-phenyl-4-hydroxypiperidide with LiAlH$_4$, in 40 ml. of acetone are heated under reflux for one hour in the presence of 0.1 g. of p-toluenesulfonic acid and the mixture is evaporated and treated with ethanolic HCl to give 2-(4-phenyl-4-hydroxypiperidinomethyl)-6,7-dimethoxy-1-tetralone hydrochloride, m.p. 175°–177°.

EXAMPLE 11

A mixture of 4.85 g. of 1,1-trimethylenedithio-2-(4-phenyl-4-hydroxypiperidinomethyl)-6,7-dimethoxytetralin, obtainable by reducing 1,1-trimethylenedithio-6,7-dimethoxy-1,2,3,4-tetrahydronaphthoic acid 4-phenyl-4-hydroxypiperidide with LiAlH$_4$, 5.43 g. of HgCl$_2$, 2.16 g. of HgO and 50 ml. of 90% methanol is heated under reflux for 90 minutes with stirring and filtered. The precipitate is washed with a little CH$_2$Cl$_2$ and the filtrate is evaporated and worked up in the customary manner to give 2-(4-phenyl-4-hydroxypiperidinomethyl)-6,7-dimethoxy-1-tetralone hydrochloride, m.p. 175°–177°.

EXAMPLE 12

3.77 g. of 2-(4-phenyl-3,4-dehydropiperidinomethyl)-6,7-dimethoxy-1-tetralone, obtainable from 6,7-dimethoxy-1-tetralone, 4-phenyl-3,4-dehydropiperidine and formaldehyde, is dissolved in 35 ml. of acetic acid. Anhydrous HBr gas is passed in at 10°–20° for 90 minutes and the mixture is allowed to stand overnight at 20°. The solution is evaporated and the resulting crude 2-(4-bromo-4-phenylpiperidinomethyl)-6,7-dimethoxy-1-tetralone hydrobromide is dissolved in 35 ml. of water and the solution is heated under reflux for 2 hours. After cooling, the pH is adjusted to 8 with potassium carbonate and the mixture is worked up in the customary manner to give 2-(4-phenyl-4-hydroxypiperidinomethyl)-6,7-dimethoxy-1-tetralone. Hydrochloride, m.p. 175°–177°.

EXAMPLE 13

3.65 g. of 2-(3-phenyl-3-buten-1-yl-aminomethyl)-6,7-dimethoxy-1-tetralone, obtainable by reducing 3-phenyl-3-butenonitrile to 3-phenyl-3-buten-1-ylamine and reacting the amine with 6,7-dimethoxy-1-tetralone and formaldehyde, are dissolved in 10 ml. of 1 N hydrochloric acid and 40 ml. of water. 1 g. of 30% formaldehyde solution is added and the mixture is stirred overnight at 80° to 90°. After cooling, the mixture is neutralized with potassium carbonate and worked up in the customary manner. The product is 2-(4-phenyl-4-hydroxypiperidinomethyl)6,7-dimethoxy-1-tetralone. Hydrochloride, m.p. 175°–177°.

EXAMPLE 14

3.81 g. of 2-(4-phenyl-4-hydroxypiperidinomethylene)-6,7-dimethoxy-1-tetralone, obtainable from 2-formyl-6,7-dimethoxy-1-tetralone and 4-phenyl-4-hydroxypiperidine, are dissolved in 30 ml. of ethanol to which 1 ml. of concentrated hydrochloric acid is added. The mixture is hydrogenated at 20° and 1 atmosphere over 0.2 g. of pre-reduced PtO$_2$. After the calculated quantity of hydrogen has been absorbed, the mixture is filtered and evaporated. The product is 2-(4-phenyl-4-hydroxypiperidinomethyl)-6,7-dimethoxy-1-tetralone hydrochloride, m.p. 175°–177°.

EXAMPLE 15

A solution of 3.98 g. of 2-(4-phenyl-4-hydroxypiperidinomethyl)-6,7-dimethoxy-1-tetralol, obtainable by reacting 2-chloromethyl-6,7-dimethoxy-1-tetralol with 4-phenyl-4-hydroxypiperidine, in 120 ml. of acetone is treated, at 0° and with stirring, with a solution of 1.28 g. of CrO$_3$ in 1.1 ml. of sulfuric acid and 3.6 ml. of water. Stirring is continued for 15 minutes more and the mixture is then stirred into ice cold sodium carbonate solution. After working up in the customary manner, 2-(4-phenyl-4-hydroxypiperidinomethyl)-6,7-dimethoxy-1-tetralone is obtained. Hydrochloride, m.p. 175°–177°.

EXAMPLE 16

3.98 g. of 2-(4-phenyl-4-hydroxypiperidinomethyl)-6,7-dimethoxy-1-tetralol, 3.1 ml. of cyclohexanone, 4.9 g. of aluminum isopropylate and 70 ml. of absolute toluene are stirred and heated under reflux for 30 hours under nitrogen. After cooling, the mixture is decomposed with water and the product is salted out with NaCl and worked up in the customary manner to give 2-(4-phenyl-4-hydroxypiperidinomethyl)-6,7-dimethoxy-1-tetralone. Hydrochloride, m.p. 175°–177°.

The examples which follow relate to pharmaceutical preparations containing active compounds of Formula I of pharmaceutically-acceptable salts thereof:

EXAMPLE A: Tablets

A mixture of 1 kg. of 2-(4-phenyl-4-hydroxypiperidinomethyl)-6,7-dimethoxy-1-tetralone hydrochloride, 40 kg. of lactose, 10 kg. of maize starch, 2 kg. of talc and 1 kg. of magnesium stearate is pressed into tablets in the customary manner so that each tablet contains 10 mg. of active compound.

EXAMPLE B: Dragees

Tablets are pressed according to Example A and coated in the customary manner with a coating consisting of sugar, maize starch, talc and tragacanth.

EXAMPLE C: Capsules 5 kg. of 2-(4-phenyl-4-hydroxypiperidinomethyl)-6,7-dimethoxy-1-tetralone hydrochloride are packed into hard gelatine capsules in the customary manner so that each capsule contains 2.5 mg. of active compound.

Tablets, dragees or capsules which contain one or more of the other compounds of Formula I or physiologically acceptable salts thereof can be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can made various changes and modifications of the invention to adapt it to various usages and conditions.

What is claimed is:

1. A tetralone or indanone compound of the formula

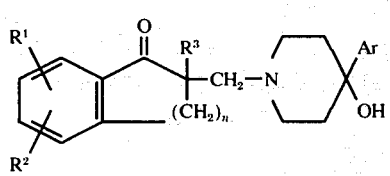

wherein $R^1$ is H, OH, alkoxy of 1–4 carbon atoms, cycloalkoxy of 3–6 carbon atoms, F, Cl, Br, $NO_2$, $NH_2$, monoalkylamino or dialkylamino, wherein the alkyl each are of 1–4 carbon atoms, alkanoyloxy of 1–6 carbon atoms or alkanoylamino of 1–4 carbon atoms; $R^2$ is H, OH, or alkoxy of 1–4 carbon atoms or $R^1$ and $R^2$ collectively are methylenedioxy; $R^3$ is H or $CH_3$; Ar is phenyl or phenyl substituted by up to 5 of alkyl or alkoxy of 1–4 carbon atoms, F, Cl, Br, or $CF_3$; $n$ is 1 or 2, and pharmaceutically-acceptable acid addition salts thereof.

2. A compound of claim 1, wherein
$R^1$ is H, OH, methoxy, ethoxy, F, Cl, Br, $NO_2$, $NH_2$, methylamino, dimethylamino or acetamido;
$R^2$ is H, OH, methoxy or ethoxy; or
$R^1$ and $R^2$ collectively are methylenedioxy.

3. A compound of claim 1, wherein
$R^1$ is H, OH, methoxy, F or Cl;
$R^2$ is H, OH or methoxy; or
$R^1$ and $R^2$ collectively are methylenedioxy.

4. A compound of claim 1, wherein $R^1$ and $R^2$ each are H or methoxy or collectively are methylenedioxy.

5. A compound of claim 1, wherein $R^1$ and $R^2$ collectively are methylenedioxy.

6. A compound of claim 1, wherein $R^1$ is H, OH, methoxy, F, or Cl; and $R^2$ is H, OH or methoxy.

7. A compound of claim 1, wherein $R^1$ is $NO_2$.

8. A compound of claim 1, wherein $R^1$ is amino, methylamino, dimethylamino or acetamido.

9. A compound of claim 1, wherein $R^3$ is H.

10. A compound of claim 1, wherein $n$ is 2.

11. A compound of claim 1, wherein $n$ is 1.

12. A compound of claim 1, wherein Ar is phenyl, tolyl, fluorophenyl, chlorophenyl, trifluoromethylphenyl or trifluoromethylchlorophenyl.

13. A compound of claim 1, wherein Ar is phenyl, p-fluorophenyl, p-chlorophenyl or m-trifluoromethylphenyl.

14. A compound of claim 1, wherein $R^1$ and $R^2$ each are H or methoxy or collectively are methylenedioxy and Ar is phenyl, tolyl, fluorophenyl, chlorophenyl, trifluoromethylphenyl or trifluoromethylchlorophenyl.

15. A compound of claim 1, wherein $R^1$ and $R^2$ each are H or methoxy or collectively are methylenedioxy, Ar is phenyl, p-fluorophenyl, p-chlorophenyl or m-trifluoromethylphenyl and $n$ is 2.

16. A compound of claim 1, wherein $R^1$ and $R^2$ each are H or methoxy or collectively are methylenedioxy, $R^3$ is H, Ar is phenyl and $n$ is 2.

17. 2-(4-Hydroxy-4-phenylpiperidinomethyl)-1-tetralone, a compound of claim 1.

18. 2-(4-Hydroxy-4-phenylpiperidinomethyl)-6,7-dimethoxy-1-tetralone, a compound of claim 1.

19. 2-(4-Hydroxy-4-phenylpiperidinomethyl)-6,7-methylenedioxy-1-tetralone, a compound of claim 1.

20. 2-(4-Hydroxy-4-m-tolylpiperidinomethyl)-6,7-dimethoxy-1-tetralone, a compound of claim 1.

21. 2-(4-Hydroxy-4-p-fluorophenylpiperidinomethyl)-6,7-dimethoxy-1-tetralone, a compound of claim 1.

22. 2-(4-Hydroxy-4-p-chlorophenylpiperidinomethyl)-6,7-dimethoxy-1-tetralone, a compound of claim 1.

23. 2-(4-Hydroxy-4-m-trifluoromethylphenylpiperidinomethyl)-6,7-dimethoxy-1-tetralone, a compound of claim 1.

24. 2-[4-Hydroxy-4-(3-trifluoromethyl-4-chlorophenyl)-piperidinomethyl]-6,7-dimethoxy-1-tetralone, a compound of claim 1.

25. 2-(4-Hydroxy-4-phenylpiperidinomethyl)-1-indanone, a compound of claim 1.

26. 2-(4-Hydroxy-4-phenylpiperidinomethyl)-2-methyl-1-tetralone, a compound of claim 1.

27. 2-(4-Hydroxy-4-phenylpiperidinomethyl)-2-methyl-6,7-dimethoxy-1-tetralone, a compound of claim 1.

28. A pharmaceutical preparation comprising a compound of claim 1, in admixture with a pharmaceutically-acceptable carrier.

29. A preparation of claim 28, wherein the compound is 2-(4-phenyl-4-hydroxypiperidinomethyl)-6,7-dimethoxy-1-tetralone hydrochloride.

* * * * *